United States Patent

Gage et al.

Patent Number: 5,922,914
Date of Patent: Jul. 13, 1999

[54] PROCESS TO PREPARE TOLTERODINE

[75] Inventors: James R. Gage, Portage, Mich.; John E. Cabaj, Sheboygan, Wis.

[73] Assignee: Pharmacia & Upjohn Company, Kalamazoo, Mich.

[21] Appl. No.: 08/993,257

[22] Filed: Dec. 18, 1997

Related U.S. Application Data

[60] Provisional application No. 60/033,961, Dec. 31, 1996.

[51] Int. Cl.⁶ .................................................. C07C 209/02
[52] U.S. Cl. ........................... 564/413; 549/399; 564/395
[58] Field of Search ........................... 549/399; 564/413, 564/395

[56] References Cited

U.S. PATENT DOCUMENTS

| | | | |
|---|---|---|---|
| 5,382,600 | 1/1995 | Jonsson | 514/603 |
| 5,482,967 | 1/1996 | Natsugari et al. | 514/457 |

OTHER PUBLICATIONS

Australian Journal of Chemistry, 26, pp. 899–906 (1973).

*Primary Examiner*—Brian M. Burn
*Attorney, Agent, or Firm*—Bruce Stein

[57] ABSTRACT

Disclosed is a novel intermediate, 3,4-dihydro-6-methyl-4-phenyl-2H-benzopyran-2-ol (IV)

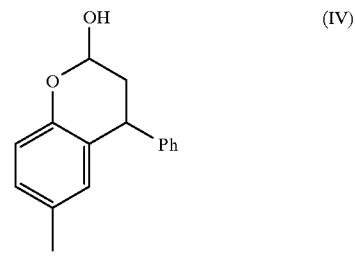

and an improved process for the preparation of tolterodine.

6 Claims, No Drawings

PROCESS TO PREPARE TOLTERODINE

CROSS-REFERENCE TO RELATED APPLICATIONS

This application claims the benefit of U.S. provisional application Ser. No. 60/033,961 filed 31 Dec. 1996, under 35 USC §119(e)(i).

BACKGROUND OF THE INVENTION

1. Field of the Invention

The invention is a process to prepare tolterodine (V) including a novel intermediate. (R)-Tolterodine L-tartrate (VI) is useful in treating urinary incontinence.

2. Description of Related Art

U.S. Pat. No. 5,382,600 discloses tolterodine (V, and its tartrate salt) together with a method for its preparation. (R)-Tolterodine (VI) is useful for treating urinary incontinence.

Australian Journal of Chemistry, 26, 899–906 (1973) discloses the lactone (III).

SUMMARY OF THE INVENTION

Disclosed is 3,4-dihydro-6-methyl-4-phenyl-2H-benzopyran-2-ol (IV).

Also disclosed is a process for the production of tolterodine (V) which comprises:
  (1) reducing the lactone (III) with a reducing agent to form the hydroxy compound (IV) and
  (2) reductively animating the hydroxy compound (IV) with diisopropylamine.

DETAILED DESCRIPTION OF THE INVENTION

U.S. Pat. No. 5,382,600 discloses tolterodine (V, and its tartrate salt) together with a method for its preparation.

The improved process for preparing tolterodine is set forth in EXAMPLES 2 and 3.

Preferred reducing agents include diisobutylaluminum hydride, sodium bis(2-methoxyethoxy)aluminum and lithium tri-tert-butyoxyaluminohydride; more preferred is diisobutylaluminum hydride (DIBAL).

It is preferred to perform the process of converting the lactone (III) to the corresponding hydroxy compound (IV) at temperatures of less than $-15°$; it is more preferable to perform this reaction at less than or equal to $-20°$.

The reaction of 4-hydroxytoluene (I) with the unsaturated acid (II) produces the lactone (III) which exists as two enantiomers. When the lactone (III) is reduced to the corresponding hydroxy compound (IV) the reduction of the carbonyl produces a secondary alcohol with an stereogenic center. Hence, there are two pairs of diastereomers. Hence, when the term 3,4-dihydro-6-methyl-4-phenyl-2H-benzopyran-2-ol (IV) is used it refers to and includes (2R,4R), (2S,4R), (2S,4S) and (2R,4S)-3,4-dihydro-6-methyl-4-phenyl-2H-benzopyran-2-ol (IV). In the transformation of the hydroxy compound (IV) to tolterodine (V), the center at 2 is lost producing tolterodine with one stereogenic center. This racemic compound is later resolved in the conversion of tolterodine (V) to (R)-tolterodine L-tartrate (VI).

Tolterodine (V) is an amine, and as such forms acid addition salts when reacted with acids of sufficient strength. Pharmaceutically acceptable salts include salts of both inorganic and organic acids. The pharmaceutically acceptable salts are preferred over the corresponding free amines since they produce compounds which are more water soluble and more crystalline. The preferred pharmaceutically acceptable salts include salts of the following acids methanesulfonic, hydrochloric, hydrobromic, sulfuric, phosphoric, nitric, benzoic, citric, tartaric, fumaric, maleic, $CH_3-(CH_2)_n-$COOH where n is 0 thru 4, $HOOC-(CH_2)n-COOH$ where n is as defined above. It is more preferred that the pharmaceutically acceptable salt of tolterodine (V) is the tartrate (VI).

(R)-tolterodine L-tartrate (VI) is known to be useful for treating urinary incontinence.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The carbon atom content of variable substituents is indicated in one of two ways. The first method uses a prefix to the entire name of the variable such as "$C_1-C_4$", where both "1" and "4" are integers representing the minimum and maximum number of carbon atoms in the variable. The prefix is separated from the variable by a space. For example, "$C_1-C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2-C_4$ alkoxycarbonyl describes a group $CH_3-(CH_2)_n-O-CO-$ where n is zero, one or two. By the second method the carbon atom content of only each portion of the definition is indicated separately by enclosing the "$C_i-C_j$" designation in parentheses and placing it immediately (no intervening space) before the portion of the definition being defined. By this optional convention $(C_1-C_3)$alkoxycarbonyl has the same meaning as $C_2-C_4$ alkoxy-carbonyl because the "$C_1-C_3$" refers only to the carbon atom content of the alkoxy group. Similarly while both $C_2-C_6$ alkoxyalkyl and $(C_1-C_3)$alkoxy$(C_1-C_3)$alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

II. DEFINITIONS

All temperatures are in degrees Centigrade.

TLC refers to thin-layer chromatography.

HPLC refers to high pressure liquid chromatography.

Chromatography (column and flash chromatography) refers to purification/separation of compounds expressed as (support, eluent). It is understood that the appropriate fractions are pooled and concentrated to give the desired compound(s).

$[\alpha]_D^{25}$ refers to the angle of rotation of plane polarized light (specific optical rotation) at 25° with the sodium D line (589A).

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

DIBAL refers to diisobutylaluminum hydride.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

3,4-Dihydro-6-methyl-4-phenyl-2H-benzopyran-2-one (III)

Trans-cinammic acid (II, 100 g, 675 mmol) is added to a 1 L 4-neck round bottom flask equipped with a mechanical stirrer, thermocouple, and nitrogen inlet. Para-cresol (I, 76.6 g, 708 mmol) is preheated in a water bath at 60° and added to the cinammic acid (II) followed by concentrated sulfuric acid (13.0 mL, 243 mmol). The reaction is immediately heated to a set point of 122.5° and stirred at 120°–125° until judged to be complete by HPLC analysis (column=nucleosil C-18; mobile phase=acetonitrile/water (45/55); flowrate=1.5 ml/min; wavelength=254 nm; sample preparation=(1) dissolve 6 drops of reaction mixture in methyl t-butylether (6 mL) pH 7 buffer, (2) dilute 0.4 mL of the organic layer in acetonitrile (5 mL) and inject;
retention times are: t-cinnamic acid=3.3 min., p-cresol=4.2 min. and the title compound=20.3 min.) or TLC (acetone/cyclohexane (20/80), acetic acid (0.5%); wavelength=254 nm) usually 6 hours. When the reaction is complete the mixture is cooled to 100° and added to a prewarmed separatory funnel (500 mL). The bottom layer containing the sulfuric acid is removed and toluene (280 mL), water (50 mL) and potassium carbonate (47%, 10 mL) are added to the separatory funnel containing the crude product. If necessary the pH of the aqueous layer is adjusted to between 5–8 with additional 47% potassium carbonate. The layers are separated and the organic layer is then washed once with water (50 mL). The organic layer is concentrated to a final volume of approximately 150 mL under reduced pressure. Isopropanol (350 mL) is then added, and distillation is continued to a volume of 350 mL. Isopropanol (150 mL) is again added and again distilled to 350 mL. Isopropanol (150 mL) is again added and again distilled to 350 mL. The mixture is then cooled to 30–40° with rapid stirring until the product crystallizes. The rapid stirring is continued after crystallization. The product is cooled to 0–5° and held at this temperature for approximately 1 hour, filtered and washed with isopropanol (200 mL) cooled to 0–5°. If the last portion of the wash is colored the wash is continued until no more color is removed. The solids are then dried at 60° under reduced pressure to give the title compound, mp (uncorrected)= 83°–85°.

Example 2

3,4-Dihydro-6-methyl-4-phenyl-2H-benzopyran-2-ol (IV)

3,4-Dihydro-6-methyl-4-phenyl-2H-benzopyran-2-one (III, EXAMPLE 1, 100.0 g, 420.2 mmol) is added to toluene (500 mL). The mixture is degassed by purging alternately with vacuum and nitrogen and then cooled to −21°. Diisobutylaluminumhydride in toluene solution (DIBAL, 1.5M, 290 mL, 435 mmol) is then slowly added over 2 hr via add funnel while maintaining the reaction temperature at −20 to −25°. The reduction is usually done when the DIBAL add is completed. If the reaction is not done additional DIBAL can be added in increments. When the reaction is done (<1% lactone) ethyl acetate (45 mL) is added at −20° to −25° via add funnel. Very little exotherm is observed. Next, citric acid (23%, 500 mL) is added. The mixture is stirred at 45–50° for 1 hr (or stirred overnight at 20–25°), the phases are separated, the organic phase is washed with water (2×300 mL). The organic phase is concentrated to 250 mL under reduced pressure. Methanol (500 mL) is added, and the mixture is concentrated to 250 mL. The methanol addition and distillation is repeated to give the title compound in methanol solution. This solution is concentrated to a thick oil which crystallizes on standing to give the title compound (as a mixture of diastereomers), IR (neat) 3410, 3020, 2925, 1605, 1498, 1447, 1205 and 1010 cm$^{-1}$; MS (m/z, EI)=240 (parent). Rather then isolating and characterizing the title compound, it is normally taken directly into the next step.

HPLC (column=zorbax C-8; mobile phase acetonitrile/water (50/50); flow rate=1 mL/min; wavelength=240 nm; note—the absorbance of the lactone (III) at 240 nm is approximately 3.5 times greater than the lactol (IV); sample preparation is (1) add 3 drops of reaction mixture to methyl t-butyl ether (1 mL) and citric acid (23%, 1 mL) and shake for approximately 1 minute, (2) wash the organic phase once with citric acid (23%, 1 mL) and once with water (1 mL), (3) dilute the organic phase (0.2 mL) in acetonitrile (1 mL) and inject; note—the methyl t-butyl ether layer must be sufficiently washed or an unknown peak at approximately 1.5 minutes will be present; retention times are: $R_t$ (diol sideproduct)=8.0 min, $R_t$ (lactol II)=15.9, 16.8 min (two diastereomers), $R_t$ (lactone III)=25.0 min.

Example 3

Tolterodine hydrochloride (V)

3,4-Dihydro-6-methyl-4-phenyl-2H-benzopyran-2-ol (IV, EXAMPLE 2, 100 g) in methanol (500 mL) is slowly added to palladium on carbon (5%, 22 g, 1.5 mmol) while maintaining a slight nitrogen purge. If 3,4-dihydro-6-methyl-4-phenyl-2H-benzopyran-2-ol (IV) is added too quickly without a nitrogen purge the catalyst will ignite the methanol. Diisopropylamine (147.0 mL, 1.05 mol) is added, and the mixture is hydrogenated at 45–50 psi and 48° until the reaction is judged to be complete by HPLC (<2% lactol). The reaction is usually done after 10 hours, but can be run overnight. The reaction mixture is cooled and removed from the hydrogenator using a methanol (150 mL) rinse. The combined reaction mixture and rinse is filtered through a bed of solka floc (10 g). The solka floc is washed thoroughly with methanol (100 mL) and the filtrate is concentrated to remove methanol while ethyl acetate is being added back. The volume of this solution of the free base of the title compound is adjusted. to 700 mL using ethyl acetate and the mixture is heated to 55°.

To form the hydrochloride salt of the title compound, concentrated hydrochloric acid (52.5 mL, 630 mmol) is added over 15 min. The resulting slurry is gradually cooled to −15° to −20° and held at this temperature for 1 hr. Tolterodine hydrochloride is collected by filtration, washed three times with ethyl acetate, and dried overnight under reduced pressure at 600 to give the title compound, mp= (uncorrected) 199–201°.

HPLC procedure is column=nucleosil C-18; mobile phase=acetonitrile/ammonium formate buffer (50/50) pH 3; flow rate=1.5 mL/min; wavelength=240 nm; retention times are $R_t$ (tolterodine)=8.7 min, $R_t$ (diol sideproduct)=7.3 min, $R_t$ (lactol III)=13.4 and 14.2 min (two diasteromers). Sample preparation is (1) dissolve 3 drops of the reaction mixture in methanol (1 mL), (2) filter through a syringe filter, (3) dilute filtered solution with acetonitrile (1 mL) and inject.

Example 4

(R)-Tolterodine L-Tartrate (VI)

Tolterodine hydrochloride (V), EXAMPLE 3, 130.0 g, 359 mmol), methylene chloride (1.3 L) and water (650 mL) are mixed. The mixture is stirred rapidly while adding sodium hydroxide (50%, 13.0 mL) and sodium carbonate (13.0 g, 123 mmol). The pH as determined by pH paper is 10–11. After stirring thoroughly for approximately 15 minutes two clear homogeneous phases form. Stirring is continued for another 45 minutes, the layers are separated and the organic phase is washed with water (2×650 mL). The methylene chloride mixture is concentrated under reduced pressure. The concentrate is dissolved in ethanol (325 mL) and warmed to 60–70°. L-tartaric acid (80.84 g, 539 mmol) slurried in hot ethanol (810 mL) is added via add funnel at 60–70° over approximately 30 minutes. When the addition is done the slurry is refluxed for 1 hr, gradually cooled to 0° and held at this temperature for 1 hr. The slurry is filtered, washed with ethanol (2×260 mL) previously cooled to 0°, and dried overnight under reduced pressure at 60° to give the crude title compound.

The crude product (136.0 g) and ethanol (5.44 L) are mixed and heated to 80° for 30 min. The mixture is concentrated to half the initial volume by distilling 2.72 L of ethanol. The mixture is gradually cooled to 20–25° over 1 hr, placed in an ice bath, and held at 0° for 1 additional hour. The tolterodine L-tartrate is collected by filtration, washed with ethanol (2×272 mL) previously cooled to 0°, and dried overnight under reduced pressure at 60° to give product. This procedure was repeated a second time on 81.0 g of once recrystallized tolterodine L-tartrate to give the optically active title compound, mp (uncorrected)=210–211°; $[\alpha]^{25}$ (1%, methanol)=27.4°.

Example 5

Preparation of (R)-Tolterodine L-Tartrate In Methanol/Acetone

Tolterodine hydrochloride (V), EXAMPLE 3, 130.0 g, 359 mmol), methylene chloride (1.3 L) and water (650 mL) are mixed. The thick slurry is stirred rapidly while adding sodium hydroxide (50%, 13.0 mL) and sodium carbonate (13.0 g, 123 mmol). The pH as determined by pH paper is 10–11. After stirring thoroughly for approximately 15 minutes two clear homogeneous phases form. Stirring is continued for another 45 minutes, the layers are separated and the organic phase is washed with water (2×650 mL). The methylene chloride mixture is concentrated under reduced pressure. The concentrate is dissolved in acetone (1.3 L), warmed to 48–50° and L-tartaric acid (80.84 g, 539 mmol) slurried in hot methanol (162 mL) is added via add funnel at 48–50° over approximately 30 minutes. The addition funnel is rinsed with acetone/methanol (90/10, 130 mL) and the slurry is refluxed for 1 hr before being gradually cooled to 0° for 1 hr. The mixture is filtered, washed with acetone (2×260 mL) previously cooled to 0°, and dried overnight in under reduced pressure at 60° to give crude (R)-tolterodine L-tartrate.

Crude (R)-tolterodine L-tartrate (115.0 g) and methanol (1.15 L) are slurried and heated to reflux for 30 min. The mixture is concentrated to half the initial volume by distilling 575 mL of methanol prior to adding acetone (3.26 L) over 30 min. The resulting slurry is refluxed for 1 hr and then gradually cooled to 20–25° over 1 hr before being placed in an ice bath and cooled to 0° for 1 additional hr. The tolterodine L-tartrate is collected by filtration, washed with acetone (2×230 mL) previously cooled to 0°, and dried overnight under reduced pressure at 60° to give tolterodine L-tartrate. This procedure was repeated a second time on 82.0 g of once recrystallized tolterodine L-tartrate to give the optically active title compound, mp (uncorrected)=210–211°; $[\alpha]^{25}$ (1%, methanol)=27.4°.

CHART A

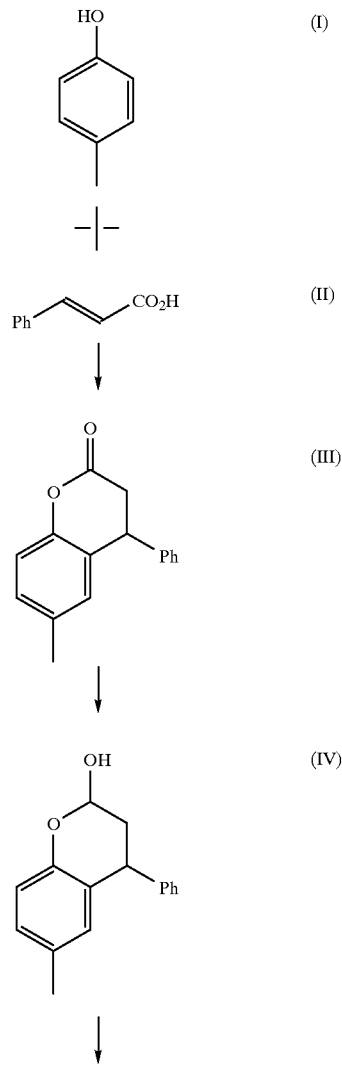

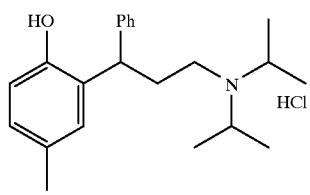

Tolterodine HCl

Tolterodine L-tartrate (VI)

We claim:
1. 3,4-Dihydro-6-methyl-4-phenyl-2H-bernzopyran-2-ol (IV).
2. A process for the production of tolterodine (V)

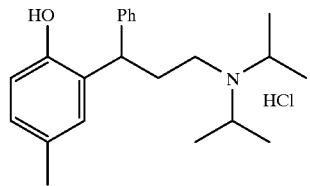

which comprises:

(1) reducing the lactone (III)

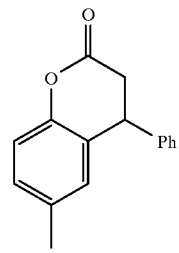

with a reducing agent to form the hydroxy compound (IV)

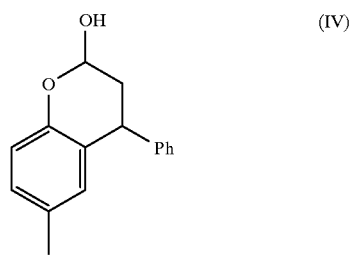

and
(2) reductively aminating the hydroxy compound (IV) with diisopropylamine.
3. A process according to claim 2 where the reducing agent is selected from the group consisting of diisobutylaluminum hydride, sodium bis(2-methoxyethoxy)aluminum and lithium tri-tert-butyoxyaluminohydride.
4. A process according to claim 2 where the reducing agent is diisobutylaluminum hydride.
5. A process according to claim 2 where step (1) is performed at less than −15°.
6. A process according to claim 5 where step (1) is performed at less than or equal to −20°.

* * * * *